United States Patent [19]

Cochran et al.

[11] 4,298,765
[45] Nov. 3, 1981

[54] PURIFICATION OF PHENOL WITH REDUCED ENERGY CONSUMPTION

[75] Inventors: Jerry R. Cochran, Chatham, N.J.; Thomas H. Insinger, Philadelphia; Gerald E. Hollenbach, Feasterville, both of Pa.; Ronald F. Piskorz, Cheektowaga; Addison M. Smith, Amherst, both of N.Y.

[73] Assignee: Allied Corporation, Morris Township, Morris County, N.J.

[21] Appl. No.: 134,040

[22] Filed: Mar. 26, 1980

[51] Int. Cl.$^3$ ............................................. C07C 37/76
[52] U.S. Cl. .................................................. 568/754
[58] Field of Search ........................... 568/754; 203/28

[56] References Cited

U.S. PATENT DOCUMENTS

| | | | |
|---|---|---|---|
| 2,864,869 | 12/1958 | Crocker et al. | 568/754 |
| 2,971,893 | 2/1961 | Hood | 568/754 |
| 3,692,845 | 9/1972 | Cheema | 568/754 |
| 3,896,006 | 7/1975 | Croke | 568/754 |

FOREIGN PATENT DOCUMENTS

| | | |
|---|---|---|
| 883746 | 12/1961 | United Kingdom . |
| 1108327 | 4/1968 | United Kingdom . |
| 1148907 | 4/1969 | United Kingdom . |

*Primary Examiner*—Werren B. Lone

*Attorney, Agent, or Firm*—Richard A. Anderson; Alan M. Doernberg

[57] ABSTRACT

Phenol (10) produced by the cleavage of cumene hydroperoxide is chemically treated with a base (12) such as a polyamine, is optionally then treated with an acid or acid anhydride (15) such as phthalic anhydride, is then steamed distilled (12) to remove a lites fraction as a water azeotrope (21) and the bottoms (34) of the steam distillation are vacuum distilled (35) to recover high purity phenol (36) as an overhead. The overheads (21) of the steam distillation are condensed (22) and may be phase separated (23) into an aqueous phase (25) and organic phase (24), with the aqueous phase (25) mixed (26) with an organic solvent (27) which preferentially dissolves benzofuran impurities. This mixture is phase separated into an organic solvent phase (30, 130) and a recycle aqueous phase (31). Alternatively, the entire condensed overheads (21) may be extracted (146-151 and 153) with organic solvent. In some forms, the organic solvent phase (130) is washed with aqueous base (142) to remove phenol and impurities and the organic solvent (127) is regenerated for again mixing with the aqueous phase. In other forms the organic solvent is a portion (152) of the high purity phenol produce (36). This treatment and careful control of the chemical treatment to minimize formation of benzofuran impurities reduces the steam consumption of the steam distillation step, thereby producing high purity phenol with reduced energy consumption.

10 Claims, 3 Drawing Figures

PURIFICATION OF PHENOL WITH REDUCED ENERGY CONSUMPTION

DESCRIPTION

BACKGROUND OF THE INVENTION

The present invention relates to the purification of phenol and particularly to the production of high purity phenol from technical or refined grade phenol which has been produced by the cleavage of cumene hydroperoxide.

A major source of phenol for many applications is the oxidation of cumene to cumene hydroperoxide and the acid cleavage of cumene hydroperoxide to a mixture of phenol and acetone which typically also contains unreacted cumene and side products such as alpha-methylstyrene, various carbonyl compounds and various benzofuran compounds. The mixture is generally subjected to a series of distillations to recover various fractions including a crude phenol fraction. Fractional distillation of the crude phenol fraction, under various conditions, produces a "technical", "refined" or water-white grade which is sufficiently pure for many purposes. Such phenol is unsatisfactory, however, for certain purposes and, in particular, when chlorinated or sulfonated with sulfuric acid, the phenol becomes red. Additionally, such phenol, itself initially gray, generally discolors on aging, becoming darker and eventually black. These effects may be due to either ketonic impurities such as mesityl oxide, acetol and acetophenone or to benzofuran impurities such as methylbenzofuran which may be formed by reaction of certain ketonic impurities such as acetol with phenol.

The purification of such technical refined grade phenol by chemical treatment is described, for example, in U.S. Pat. No. 3,692,845 to Cheema et al. (Sept. 19, 1972); U.K. Pat. No. 883,746 to National Distillers Company (Dec. 6, 1961); U.S. Pat. No. 2,864,869 to Crocker et al. (Dec. 16, 1958); U.K. Pat. No. 1,108,327 to Universal Oil Products Company (Apr. 3, 1968); U.K. Pat. No. 1,148,907 to Imperial Chemical Industries Limited (Apr. 16, 1969) and U.S. Pat. No. 2,971,893 to Hood (Feb. 14, 1961). The present invention is applicable to processes of purification which include treatment of the phenol with a base such as alkali metal hydroxides or carbonates or monoamines or diamines as described in U.K. Pat. No. 883,746 or hydrazines as described in U.S. Pat. No. 2,864,869 or alkaline hydrogen peroxide as described in U.S. Pat. No. 2,971,893. The present invention is especially applicable to processes of purification which include treatment with polyamines followed by the addition of acid or acid anhydride followed by distillation as described in U.S. Pat. No. 3,692,845. The present invention also includes steam and product distillations as separate steps, which are also described as separate steps in U.K. Pat. No. 883,746 and U.S. Pat. No. 2,971,893.

The object of the present invention is to achieve phenol of high purity from technical or refined grade phenol or from impure phenol streams with a minimal use of energy, and especially a minimal use of steam in the steam distillation. This is accomplished by careful control of the chemical treatment to minimize the formation of certain hard to separate impurities during the treatment and by extraction of the overheads of the steam distillation.

BRIEF DESCRIPTION OF THE INVENTION

The present invention includes an improvement in the process of purifying phenol produced by the cleavage of cumene hydroperoxide wherein phenol is treated with a base, optionally an acid or acid anhydride is added, the treated phenol is steam distilled to remove a lites fraction as a water azeotrope and the bottoms of the steam distillation are distilled to recover high purity phenol as an overhead. In the improvement, the overheads of the steam distillation are condensed and phase separated into an aqueous condensate phase and an organic condensate phase, organics are extracted from the aqueous condensate phase with an organic solvent which preferentially dissolves benzofuran impurities to produce a reflux aqueous phase, and the reflux aqueous phase is returned to the steam distillation.

In one form of the present invention the organic solvent is a material other than phenol, such as cumene; and the organic solvent after extraction is washed with aqueous base to remove phenol. The organic solvent is separated from the impurities (e.g. by distillation) and used to extract additional organics from the aqueous condensate phase. In another form of the invention, the organic solvent is a portion of the high purity phenol.

DETAILED DESCRIPTION OF THE INVENTION

Figure 1:
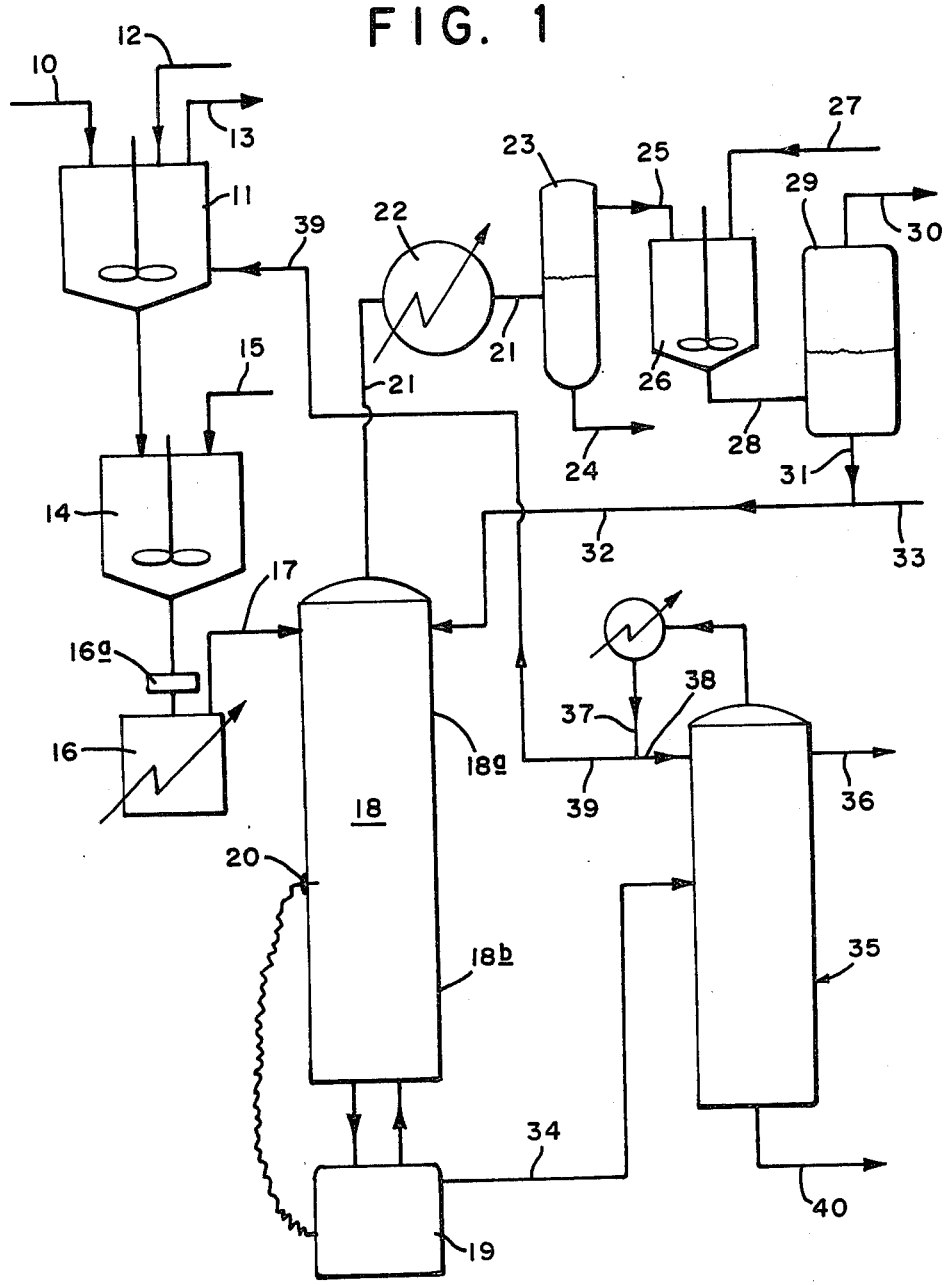

The phenol used as feed in the present process is produced by the cleavage of cumene hydroperoxide. It may be the technical or refined grade phenol normally produced as one distillation product from such a process. It may also be one or more impure phenol streams found in plants for the production of phenol containing water, containing coproduct acetone, containing unoxidized cumene, containing alpha methyl styrene (a byproduct), containing various high boiling impurities such as dimethylphenylcarbinol. The phenol may contain certain difficult to separate impurities, which are principally methyl benzofuran and ketonic impurities such as acetol, mesityl oxide and acetophenone. In general, the normal refined grade phenol is low in overall impurities (under 5000 ppm) but has relatively high levels of the impurities hardest to separate: methylbenzofuran (50–150 ppm), acetophenone (75–2000 ppm), acetol (1000–4000) and other ketonics (100–500). Various phenol-containing streams are produced (for example in residue reforming and dephenolization of waste water) which have substantial water contents (5–20%) and high total organic impurity levels (10,000–30,000 ppm) but may have lower levels of methylbenzofuran (generally under 100 ppm).

As illustrated in the examples that follow, various such phenol streams can be used in the present process, thereby not only producing high purity phenol of better quality than refined grade phenol, but also reducing the requirements for batch stills and the like to purify various other phenol streams. It should be appreciated that many of these other streams are currently purified by distillation to produce a product lower in overall quality than refined grade phenol.

If water is present in the feed, it is easily removed by evaporation from the phenol during the chemical treatment with the base. Some phenol is removed thereby as the water:phenol azeotrope. This phenol may be recovered by combining the azeotrope with the azeo stripper overheads for solvent extraction.

It might be possible to construct a purification system from the prior art that followed chemical treatment of refined grade phenol with azeotropic distillation with water and then vacuum distillation to recover the product high purity phenol as an overhead stream. Such a process, assuming that the aqueous condensate (containing methylbenzofuran) was returned to the first (azeotropic distillation) column, would require large amounts of water (and thus energy for reboiling) compared to phenol feed to the first column. For example, one such experiment required 2.6–3.0 parts of water by weight for each part of refined phenol. If the aqueous condensate (containing methylbenzofuran) is not returned to the column, a smaller fresh water ratio could be used, such as about 1 part water per part of refined phenol in comparable experiments. Such a fresh water process would generate undesirable amounts of phenol-contaminated water which must be treated to remove organics.

In the present process, by extracting organics from the aqueous condensate or from the entire condensate (containing methylbenzofuran) in either case before returning the aqueous condensate to the column, a ratio close to that achieved by feeding fresh water to the column has been achieved. Thus, with cumene as the organic extractant, the same quality phenol was obtained using a water to phenol feed ratio of about 1.2:1. With high purity phenol as the extractant, a ratio of about 1:1 was achieved in comparable experiments. Of course it should be appreciated that the level of certain impurities such as methylbenzofuran is directly linked for each system to the water:phenol feed ratio in the column, such that experiments can be considered comparable only if they achieve equivalent low levels of such impurities in the stream removed from the bottom of the first still.

The phenol removed with impurities during solvent extraction or the phenol from high purity phenol extractions can be recovered by treating with aqueous sodium hydroxide. For the solvent extraction process, the impurities are concentrated in the solvent phase. For the high purity phenol extractions, solvent extraction of the aqueous sodium hydroxide-phenol solution is required.

In addition to the use of extraction before returning the aqueous condensate, two other improvements are preferably made in the overall process. First the azeotropic distillation column is preferably controlled (as by the sensor control on the reboiler illustrated in FIG. 1) so that the control temperature is at or near the boiling point of phenol. As a result, this portion of the column dehydrates the phenol since a separation between phenol-water azeotrope and phenol vapor can occur. Second, the chemical treatment is preferably conducted with a polyamine followed by phthalic acid acidification to a pH of about 4.0 to about 5.5 to prevent formation of methylbenzofuran during chemical treatment.

DESCRIPTION OF THE PREFERRED EMBODIMENTS

Referring to FIG. 1, phenol from a cumene hydroperoxide cleavage process in stream 10 is charged to a treatment apparatus 11 equipped with agitation along with a base in stream 12. Exemplary of the base is either 5 molar sodium hydroxide, 100 weight percent hexamethylene diamine or 70 weight percent aqueous polymeric hexamethylene diamine such as is sold by E. I. du Pont de Nemours as Du Pont Amine 248. The temperature and residence time in apparatus 11 should be sufficient to complete the desired chemical treatment and tie up various impurities. A residence time in apparatus 11 of 1 hour to 5 hours is generally sufficient, with shorter residence times as small as a few minutes being satisfactory for certain polyamines. Temperatures of above 100° C. such as 150°–180° C. are preferred.

If the phenol fed in stream 10 contains significant amounts of water or low boiling impurities such as cumene, acetone and alpha methyl styrene, they will evaporate off in treatment apparatus 11 and can be conveniently removed, preferably after passing through a simple still to minimize entrained organics, through stream 13 for treatment as with other low boiling mixture produced in phenol manufacture.

From apparatus 11, the mixture is conducted to acidification vessel 14 where an acid or acid anhydride such as phthalic anhydride is added in stream 15. Such acid treatment may not be required in the case of many bases introduced through stream 12, but is generally desirable, especially when monoamines, diamines, or other polyamines are used as the base. It is preferred that the acid or anhydride in stream 15 lower the pH of the liquid in vessel 14 to a pH no lower than about 4.0 and preferably to a pH of between about 5.0 and about 5.5 to prevent formation of additional methylbenzofuran. In the Examples, phthalic anhydride was fed into the acidification vessel as a solution dissolved in high purity phenol.

From acidification vessel 14, the mixture is passed through filter 16a, preheater 16 and stream 17 into the first still 18 in which it is steam distilled. The recovered azeo water after extraction, stream 32, can be combined with the chemically treated phenol fed to preheater 16 and fed through stream 17 to the first still 18. Heat is supplied to reboiler 19 of still 18 in a conventional manner. Reboiler 19 is controlled by a thermal sensor 20 so as to maintain a constant temperature at a level in still 18 slightly above the boiling point of phenol, such as 185°–195° C., preferably 186°–190° C. (assuming that still 18 is at about atmospheric pressure). The effect is to cause still 18 to perform two functions: Azeotropic distillation in section 18a above sensor 20 and dehydration in section 18b below sensor 20.

An overhead stream 21 is continuously withdrawn from the still 18 above the top plate or tray, and a bottoms stream 34 is continuously withdrawn from the reboiler 19 of still 18.

Figure 3:
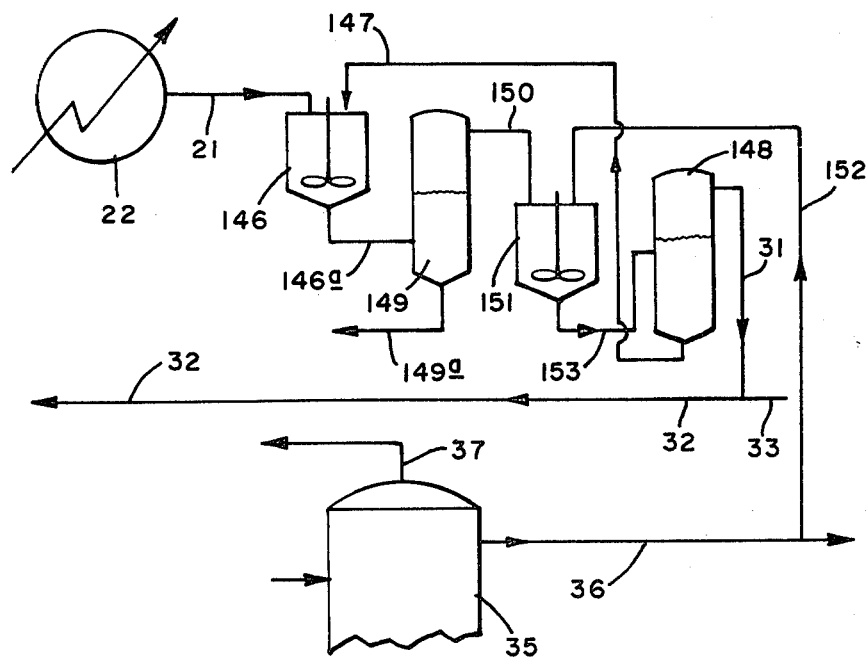

The overhead stream 21 of the first still 18 is condensed in condenser 22 where it is cooled to a temperature such as 25°–50° C. and may then be fed to a separation vessel 23 where it is permitted to separate into an organic condensate phase and an aqueous phase. The organic condensate phase is withdrawn from the bottom of vessel 23 in stream 24 since phenol which comprises the major portion of the organic phase is denser than water. The aqueous condensate phase (containing both methylbenzofuran and phenol dissolved in water) from vessel 23 is withdrawn in stream 25 to a mixing vessel 26 where it is mixed with an organic solvent, stream 27, to extract organics from stream 25. Alternatively, the entire condensed overheads in stream 21 may be passed to mixing vessel 26, especially if the solvent in stream 27 is high purity phenol as illustrated in FIG. 3, discussed below. The mixture in vessel 26 is then fed in stream 28 to a second separation vessel 29 where it is again separated into an organic phase (now called the organic solvent phase) in stream 30 and an aqueous phase (now called the aqueous recycle phase) in stream 31. As illustrated, the organic solvent phase is assumed to be less dense than the aqueous phase (as is the case with cumene) such that it can be withdrawn from the top of vessel 29 in stream 30 and the aqueous recycle phase can be withdrawn from the bottom of vessel 29 in stream 31. If the organic solvent phase is denser, however, the locations of streams 30 and 31 would be reversed. The aqueous recycle phase in stream 31 is fed back through stream 32 into the still 18.

It is desirable to reheat the aqueous recycle before introducing it back into still 18. Therefore stream 32 may be introduced into preheater 16 along with the mixture from acidification vessel 14. Alternatively, the recycle water (in stream 32), the mixture (from vessel 14) or both may be passed through condensor 22 in heat exchange with overheads so as to perform a part of the processes of preheating these streams and of cooling and condensing the overheads.

A stream 33 is provided to either add or withdraw water from stream 32 as is required to maintain a controlled or constant water content in still 18. It should be appreciated that the amount of water charged into the system through streams 10, 12 and 15 and the amount of water withdrawn from the system in streams 13, 24, 30 and 34 are sufficiently variable that, in some cases, make up water through stream 33 will be required while, in other cases, a portion of stream 32 must be diverted out of the system through stream 33 to avoid water build up.

The bottoms from the reboiler 19 of still 18 in stream 34 are fed to a vacuum product still 35 which may be operated at 50–200 torr pressure (about 0.06–0.26 atmospheres). Product high purity phenol is removed in stream 36 from vacuum still 35 near, but preferably not at the top. A small pasteurizing cut is preferably taken from the condensed overhead vapors 37 taken from the top of still 35, which are returned as reflux 38. A portion of the pasteurizing cut in stream 37 is recycled in stream 39 to treatment vessel 11. Material in stream 39 may alternatively be returned to the first still 18 directly or indirectly, by introduction into neutralization vessel 14 or preheater 16.

The bottoms from vacuum still 15 are withdrawn in stream 40. Some phenol of various grades may be recovered from these bottoms in a conventional manner.

Figure 2:
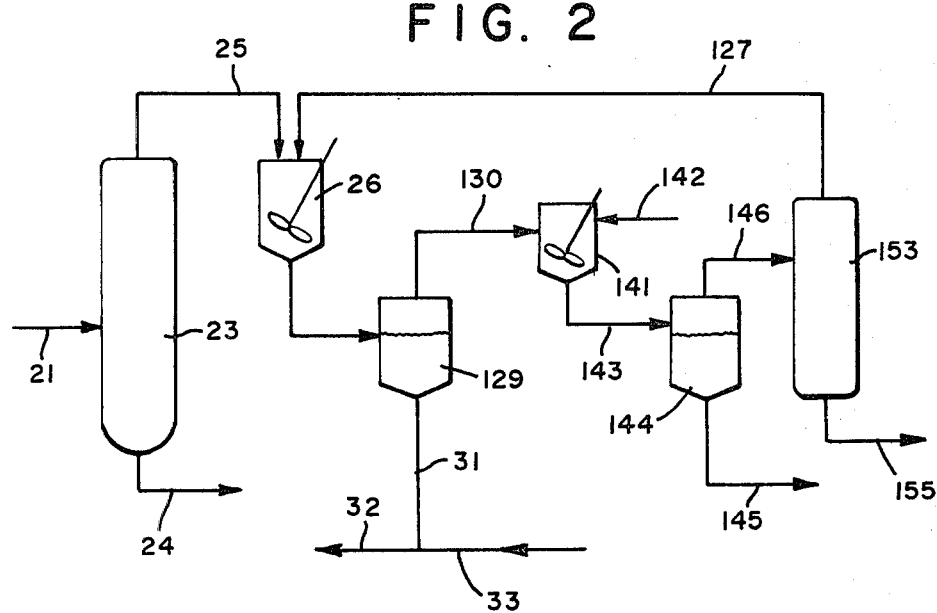

FIG. 2 shows a modified form of the condensate extraction represented by elements 26–31 in FIG. 1. Elements 21 and 23–26 in FIG. 2 are identical to the corresponding elements in FIG. 1.

Thus the aqueous condensate (containing both methylbenzofuran and phenol) in separation vessel 23 is conveyed in stream 25 to mixing vessel 26 where it is mixed with an organic solvent (for removal of these organics) introduced now through stream 127. From mixing vessel 26, the mixture passes in stream 128 to separation vessel 129 where it is separated into an aqueous recycle phase (illustrated as the more dense phase) and an organic solvent phase (illustrated as the less dense phase). The aqueous recycle phase is returned to the azeotropic still 18 via streams 31 and 32 with water added or removed through stream 33 as in FIG. 1.

The organic solvent phase in separation vessel 129 is conveyed through stream 130 to mixing vessel 141 where it is mixed with strong aqueous base such as sodium hydroxide introduced through stream 142. The mixture is then removed through stream 143 to separation vessel 144 where it is separated into a solvent phase (illustrated as less dense than water) and an aqueous phase (removed in stream 145) that will contain most of the phenol in the organic solvent phase of stream 130, now as a water soluble phenate such as sodium phenate. This phenol can be sprung by adding concentrated sulfuric acid, separating phases and returning the water-saturated phenol to stream 17.

The organic layer in separation vessel 144 contains impurities which must be removed from the solvent. The organic phase is conveyed through stream 146 to distillation column 153. Pure organic solvent is removed overhead and returned via stream 127 to mixing vessel 26. Some make-up solvent can be added if needed. Organic impurities are removed from the process through stream 155.

The embodiment of FIG. 2 utilizes a solvent such as cumene or toluene to extract phenol from the aqueous condensate layer before returning it to the azeo still. This phenol is removed from the solvent by conversion to a water-soluble phenate. Pure solvent is recovered for recycle by distillation.

In both FIGS. 1 and 2, various impurities such as methylbenzofuran, acetone, mesityl oxide and cumene are removed from the system in stream 24 and also by extraction of the aqueous condensate.

Referring now to FIG. 3 a further modified system is shown in which the condensed overheads of stream 21 from the azeotropic still 18 are charged directly to mixing vessel 146. Alternatively, phase separation in vessel 23 shown in FIGS. 1 and 2 could be performed and the aqueous layer in stream 25 would then be charged to mixing vessel 146.

This condensate (or aqueous layer) is not mixed directly with the organic solvent, which in this case is high purity phenol from the product stream 36, but is rather mixed in mixing vessel 146 with the organic phase in stream 147 from a separation vessel 148. Mixture from mixing vessel 146 is charged to another separation vessel 149 through stream 146a. The organic layer in vessel 149 is withdrawn through stream 149a and (like the organic condensate layer in stream 24 if vessel 23 is used) withdrawn.

The aqueous layer from separation vessel 149 is conveyed in stream 150 to mixing vessel 151. A portion of product high purity phenol from product still 35 in stream 36 is diverted in stream 152 to mixing vessel 151. The mixture from mixing vessel 151 is conveyed in stream 153 to separation vessel 148, where it is separated into an organic phase (conveyed to mixing vessel 146 in stream 147) and an aqueous recycle phase. The aqueous recycle phase is conveyed in streams 31 and 32 back to the first or azeotropic still 18, with water added or removed if needed through stream 33, as in FIGS. 1 and 2.

The system of FIG. 3 utilizes high purity phenol to extract impurities in two stages from the aqueous condensate of stream 25. Depending upon residence times, impurity levels and other factors, more or less than two stages may be required. The efficiency of the system is based upon the preferential solubility of certain hard to remove impurities in the high purity phenol (such that they migrate to the organic phases in separation vessels 148 and 149) compared to their lesser solubility in the aqueous layer in separation vessels 148 and 149 (and 23 if used). The advantages of the high purity phenol extraction, particularly of the entire condensed overheads, are that most of the phenol is not lost with a solvent such as cumene and that the relatively slow phase separation in vessel 23 can be avoided.

EXAMPLES

Feed phenols—Aliquots of the phenol batches used as feed materials in the chemical treatment step of the following Examples were analyzed by gas chromatography for impurities. Some 10–15 peaks were identified, with nine assigned definite structures. The first 5 samples are considered technical grade phenol and generally have 1000–5000 ppm total impurities. Analyses produced the results (in ppm) shown in Table 1.

TABLE 1

| | Refined Phenol Starting Materials | | | | | | | | |
|---|---|---|---|---|---|---|---|---|---|
| Impurity | Acetone | MO | Cumene | Acetol | AMS | MBF | AP | DP | Other |
| Phenol Sample (total impurities) | | | | | | | | | |
| A (1844) | 3 | 174 | 13 | 1278 | 116 | 57 | 84 | 0 | 119 |
| B (2622) | 16 | 352 | 25 | 1623 | 128 | 51 | 219 | 0 | 208 |
| C (3326) | 4 | 340 | 11 | 2058 | 72 | 52 | 711 | 0 | 78 |
| D (5066) | 9 | 327 | 61 | 3392 | 162 | 104 | 669 | 0 | 342 |
| E (5765) | 9 | 426 | 45 | 3233 | 260 | 104 | 1270 | 25 | 373 |

O = mesityl oxide
Acetol = hydroxyacetone
AMS = Alpha methyl styrene
MBF = methylbenzofuran
AP = Acetophenone or methylphenyl ketone
DP = dimethylphenylcarbinol Other materials used were a plant process stream known as "pink phenol", a plant process stream known as "sprung phenol", a 70/30 blend of the two by volume and the product of dehydration of the 70/30 blend by removal of 15.5 weight % by evaporation at 160° C. and one atmosphere pressure. Analyses of these other materials (in ppm except for water) are shown in Table 2.

TABLE 2

| | Other Starting Materials | | | | | |
|---|---|---|---|---|---|---|
| Impurity | MO | Acetol & AMS | AP | MBF | Other | Water |
| Phenol Sample (total impurities except water) | | | | | | |
| Pink Phenol (4700) | 30 | 1279 | 2,283 | ND | 1,108 | 2.15% |
| Sprung Phenol (26,000) | 72 | 1850 | 10,600 | 189 | 13,289 | 16.4% |
| 70/30 (26,700) | 84 | 2126 | 10,400 | 124 | 13,966 | 12.13% |
| Dehydrated 70/30 (15,300) | 44 | 2168 | 10,900 | 130 | 2,058 | NM |

ND = not detectable
NM = not measured

Example 1

In a 22 L round bottom flask, phenol sample B (having 2622 ppm total impurities of which 2194 ppm were carbonyls and 51 ppm were MBF) was treated by heating to 160° C. and adding 0.2194% hexamethylenediamine (HMDA) by weight of phenol (0.1% per 1000 ppm of total carbonyl impurities). Treatment was continued for 4 h at 160° C. under a nitrogen atmosphere with agitation. Phthalic anhydride (PAA) was then added in small increments until the pH was down to 5.5. Phenol aliquots dissolved in water (5% solutions) were used to measure pH. 0.185% PAA by original weight of phenol was added. Gas chromatographic analysis of the treated phenol before and after acid addition showed 455 ppm total impurities (36 ppm MBF) before acidification and 470 ppm total impurities (46 ppm MBF) after acidification.

The treated phenol as described above, and phenol from similarly treated 3–5 L batches, were azeotropically distilled in a 1 inch (2.5 cm) by 51 tray Oldershaw column. The column was assembled from 1, 5, 10 and 20 tray sections with the treated phenol and water fed at the 50th tray. Azeotrope overheads were removed by a total condenser above the 51st tray and still bottoms removed from the bottom of the reboiler. The reboiler had an electrical heating element controlled by a thermosensor to sense and maintain a selected temperature in the range of 180° C. to 186° C. at a location, in most runs, above the fifteenth tray. The conditions for these runs are displayed in Table 3.

TABLE 3

| | Azeotropic Distillations With Fresh Water | | | |
|---|---|---|---|---|
| Azeo Run | Phenol MBF Conc. After Chem. Treatment | Water:Phenol Feed Ratio (total g:g) | Overheads (% phenol removed overhead) | Azeo Bottoms (Total Impurities/ MBF in ppm) |
| A | (51 ppm)* | 1.07:1 (800:750) | 874.3 g (12.0–12.6%) | 660.2 g (110/12) |
| B | #4 (46 ppm) | 0.95:1 (1278:1345) | 1415 g (10.2%) | 1208 g (116/21) |
| C | #4 (46 ppm) | 1.09:1 (1300:1197) | 1435 g (12.0–11.3%) | 1054 g (110/21) |
| D | (37 ppm)* | 1.01:1 (1510:1493) | 1681 g (12.7–11.5%) | 1303 g (58/3.0) |

*HMDA treated phenol only. No acidification with PAA. This material had a poor shelf life, developing a pink color rapidly.

The % phenol in the overheads was calculated from analyses of the bottoms and of the overheads. Where these values differ, they are both shown in Table 3.

The bottoms from these four azeo stripper runs were separately batch distilled in a one inch (2.5 cm) diameter by 20 plate Oldershaw column. A controlled vacuum source set at 100 mm of mercury (13.3 kPa) and a water cooled condenser (at 40° C.) above the reflux splitter were used. A lites or pasteurizing cut was taken prior to collecting the high purity phenol fraction. These product distillations are summarized in Table 4, Runs A–D.

TABLE 4

Product Distillations

| Product Run | Azeo Bottoms Impurities Total/MBF (in ppm) | % Lites as Pasteurizing Cut | % Main High Purity Phenol | Main Cut Impurities (in ppm) Total | MBF |
|---|---|---|---|---|---|
| A | 110/12 | 2.94 | 92.7 | 26 | 10 |
| B | 116/21 | 5.2 | 91.0 | 20 | 10 |
| C | 110/21 | 3.5 | 94.90 | 17 | 10 |
| D | 58/3.0 | 2.5 | 94.1 | 17 | 2 |
| E | 66/10 | — | 99 | 31 | 10 |
| F | 80/16 | 5.9* | 93 | 14 | 4 |
| G | 74/14 | 2.5* | 97 | 8 | 5 |

*In runs E, F & G, a continuous distillation column was used which included a second reflux splitter separated from the first by a 10 inch (25 cm) Vigereux section. Pasturizing cuts were removed from the reflux splitter installed above the Vigereux section in runs F & G. Main (product) cuts were removed using the reflux splitter installed below the Vigereux section.

Example 2—Production of High Purity Phenol Using Extracted Recycle Water

The azeotropic and product distillations of Example 1 were repeated using, for the azeotropic distillation, cumene extracted aqueous condensates from previous runs. Thus overheads from a run were collected and allowed to phase separate. The aqueous layer was extracted three times using a cumene azeo water weight ratio of 0.5:1 (or volume ratio of 0.43:1). After phase separation, an aliquot of the aqueous layer from the third separation was analyzed for phenol and impurities. All of the MBF was selectively removed by the cumene extractions. Approximately 80% of the dissolved phenol and other organics were also removed. A larger sample of this aqueous layer was then used as feed water for the following distillations. The azeotropic distillations are shown in Table 5.

TABLE 5

Azeotropic Distillations With Cumene-extracted Recycle Water

| Azeo Run | Phenol-MBF Concentration After Chemical Treatment | Water: Phenol (Total g:g) | Overheads (% phenol removed overhead) | Bottoms (total imp/MBF in ppm) |
|---|---|---|---|---|
| E | 227 ppm | 1:1 (973: 968) | 1042 g (7.1%) | 899 g (214/74) |
| F | 88 ppm | 1.01:1 | 824 g (10.3–10.0) | 664 g (172/31) |
| G | 45 ppm | 1.19:1 (1603: 1346) | 1710 g (11.0–8.0) | 1198 g (76/14) |
| H | 45 ppm | 1.18:1 (1239: 1050) | 1347 g (11.7–10.3) | 927 g (101/17) |
| J | 45 ppm | 1.05:1 (1239: 1050) | 1365 g (11.9–9.3) | 1055 g (79/16) |
| J | 45 ppm | 1.03:1 (1070: 1044) | 1174 g (9.96) | 940 g (78/10) |
| K | 45 ppm | 1:1 (1639: 1647) | 1811 g (11.5–10.5) | 1458 g (78/15) |
| L | 45 ppm | 1.14:1 (2045: | 2261 g (11.83–11.96) | 1584 g (81/18) |

TABLE 5-continued

Azeotropic Distillations With Cumene-extracted Recycle Water

| Azeo Run | Phenol-MBF Concentration After Chemical Treatment | Water: Phenol (Total g:g) | Overheads (% phenol removed overhead) | Bottoms (total imp/MBF in ppm) |
|---|---|---|---|---|
| | | 1797) | | |

The azeo bottoms fractions from the above runs were subjected to batch distillation as in Example 1. The azeo bottoms sample from Run G was used for two separate product distillations, Runs I and H (with and without pasteurizing cut). A pasteurizing or lites cut was also not obtained for azeo bottoms from azeo distillation Run J in batch product distillation Run L. The results are shown in Table 6.

TABLE 6

Product Distillations

| Product Run | Azeo Bottoms Impurities (in ppm) Total/MBF | % Distilled as Lites | % Main | Main Cut Impurities (in ppm) Total | MBF |
|---|---|---|---|---|---|
| H | 76/14 | 0 | 96.1 | 12 | 5 |
| I | 76/14 | 7.6 | 91.1 | 14 | 7 |
| J | 101/17 | 3.9 | 93.0 | 10 | 4 |
| K | 79/16 | 3.0 | 90.0 | 20 | 8 |
| L | 78/10 | 0 | 97.0 | 21 | 9 |

In the next azeotropic distillation (azeo Run M) phenol with 104 ppm MBF impurity was used; a (high purity phenol extracted) water:phenol feed ratio of 0.99:(1344 grams to 1356 grams) was employed; 1478 g of material was removed overhead (containing 9.0% of the phenol feed); and 1195 g of material was removed as bottoms (containing 195 ppm total impurities including 3 ppm MBF). In the subsequent batch product distillation (Product Run M) 4.3% of the material distilled was removed as a pasteurizing cut and 89.7% as the main or product cut. The product cut contained 10 ppm total impurities (5 ppm MBF) compared to 195 ppm total impurities (3 ppm MBF) in the azeo bottoms fed to the product distillation column.

Example 3—Production of High Purity Phenol Using Low Grade Starting Materials

A 1513 g sample of the dehydrated 70/30 mixture described above in Table 2 was chemically treated at 160° C. with HMDA for ten hours. HMDA was added slowly over ten hours, with 2.5 g HMDA having been added by two hours (pH 5.45), 4.95 g HMDA having been added by four hours (pH 7.1) and 12.3 g HMDA having been added after ten hours (pH 7.5). Each pH measurement was obtained by making a 5% aqueous solution of phenol from a sample from the chemical treatment. PAA was then added to adjust the pH down to 5. Aliquots were taken before any HMDA addition and at 2 h, 4 h and 10 h and after PAA addition. The results of analyses (in ppm) of these aliquots are displayed in Table 7.

TABLE 7

Chemical Treatment of Low Grade Phenol

| Aliquot | Total Impurities | MO | Acetol & AMS | AP | MBF |
|---|---|---|---|---|---|
| Initial | 15,300 | 44 | 2168 | 10,900 | 130 |
| 2 h | 15,300 | 19 | 0 | 10,900 | 133 |

TABLE 7-continued

| | Chemical Treatment of Low Grade Phenol | | | | |
|---|---|---|---|---|---|
| Aliquot | Total Impurities | MO | Acetol & AMS | AP | MBF |
| 4 h | 13,200 | ND | 0 | 10,700 | 105 |
| 10 h | 12,800 | ND | 0 | 10,700 | 69 |
| After PAA | 12,700 | 10 | 0 | 10,700 | 77 |

A larger batch was then chemically treated in like manner, except that after HMDA addition to a pH of of 7.1, the treatment was limited to 4 h at 160° C. PAA was then added to adjust the pH to 5. Four samples of the resultant treated material were then subjected to azeotropic distillation as in Example 1 using fresh water feed. The results are displayed in Table 8.

TABLE 8

| Azeo Run | Phenol MBF After Chemical Treatment (ppm) | Water:Phenol (total g:g) | Overheads (% Phenol Removed As Overheads) | Azeo Bottoms (Total Imp in ppm)* |
|---|---|---|---|---|
| N | 64 | 1.14:1 (450:415) | 467 g (11) | 411.2 g (9870) |
| P | 64 | 1.03:1 (760:739) | 873 g (14–15) | 648 g (9756) |
| Q | 64 | 2.13:1 (580:296) | 648.2 g (23.1) | 227.2 g (9579) |
| R | 64 | 1.91:1 (1146:600) | 1285 g (23.3) | 460.0 g (8541) |

*MBF concentration of azeo bottoms could not be established due to interference of unknown impurities. Total impurities represent an average of several samples.

The 648 g bottoms of azeo Run P and the 227.2+460.0 g combined bottoms of azeo Runs Q and R were batch distilled as in Example 1. The results are shown in Table 9.

TABLE 9

| | | Product Distillations | | | |
|---|---|---|---|---|---|
| Product Runs | Feed Impurities Total | % Lites as Pasteurizing Cut | % Main | Main Cut Impurities Total | MBF |
| N | 9756 | 4.0 | 86.5 | 16 | 2.4 |
| P | 8884* | 3.0 | 87.0 | 18 | 0 |

*calculated as $\frac{(227.2 \times 9579) + (460.0 \times 8541)}{227.2 + 460.0} = 8884$ The product main cut from Product run N contained 16 ppm total impurities (2.4 ppm MBF). The pasteurizing cut from Product Run N contained 1010 ppm total impurities including 27 ppm of a contaminant having the same elution time as MBF. Previous studies have indicated that MBF cannot be separated from phenol by a simple vacuum distillation. The peak eluting as MBF in the pasteurizing cut is probably some other impurity. The results of these experiments indicates that azeotropic distillation using a 1:1 feed ratio of chemically treated low grade phenol(s) to fresh water is adequate to obtain a high purity phenol product.

Example 4

Using the dehydrated 70/30 mixture and the chemical treatment of Example 3, four azeotropic distillations (with fresh water) were conducted as described in Table 10. The chemically treated phenol feed had 14,570 ppm total impurities including 64 ppm MBF. The impurity levels of the azeo bottoms has not yet been determined.

TABLE 10

| Azeo Run | Water:Phenol Feed Ratio (total g:g) | Overheads (% phenol feed removed overhead) | Azeo Bottoms |
|---|---|---|---|
| S | 0.95:1 (833.880) | 922.8 g (12.1–9.7) | 773.5 g |
| T | 0.97:1 (840:862.5) | 945.0 g (11.9–11.1) | 760.0 g |
| U | 0.96:1 (831.4:870) | 932.0 g (14.6–10.8) | 743.0 g |
| V | 0.95:1 (880:924) | 968.0 g (14.1–9.1) | 794.0 g |

The azeotropic still bottoms were combined into two samples and each of the two was batch distilled by the process used in Examples 1 and 4. These distillations are summarized in Table 11. Product Run Q used azeo bottoms from Azeo Runs S and T. Product Run R used azeo bottoms from Azeo Runs U and V.

TABLE 11

| Product Run | Feed Impurities Total | % Lites as Pasteurizing Cut | % Main HP Phenol | Main Cut Impurities in ppm Total | MBF |
|---|---|---|---|---|---|
| Q | N.A. | 4.2 | 87.1 | 22.8 | 1.0 |
| R | N.A. | 3.0 | 87.8 | 20.4 | 1.6 |

The overheads from azeotropic distillations S, T, U and V shown in Table 10 were phase separated and the aqueous layers composited. Approximately 3500 g of azeo water was collected. Analysis of the phenol saturated aqueous layer indicated 1100 ppm of dissolved impurities. 400.2 g of this aqueous condensate were extracted three times at 40° C. with 20.6 g each of high purity phenol containing 16 ppm total impurities (9 ppm acetone, 7 ppm others). A 16.0 g phenol layer and 404.8 g aqueous layer were recovered from the first extraction (with a 2.0 g sample of the aqueous layer removed before the second extraction). A 30.5 g phenol layer and a 392.3 g aqueous layer were recovered from the second extraction (with a 2.0 g sample removed before the third extraction). A 33.7 g phenol layer and a 379.4 g aqueous layer were recovered from the third extraction (again a 2.0 g sample was removed). Analyses of the three recovered phenol layers and three aqueous layers (impurity levels in ppm) are displayed in Table 12.

TABLE 12

| After Extraction | Phase | Total Impurities | Acetone | MBF | AP | Others |
|---|---|---|---|---|---|---|
| 1 | Phenol | 7564 | 4433 | 49.6 | 2576 | 505 |
| 2 | Phenol | 3873 | 3200 | 12 | 539 | 122 |
| 3 | Phenol | 2342 | 2195 | ND | 112 | 35 |
| 1 | Aqueous* | 713 | 656 | 1 | 45 | 11 |
| 2 | Aqueous* | 485 | 473 | 0.3 | 10 | 2 |
| 3 | Aqueous* | 300 | 297 | 0.4 | 2 | 1 |

*also saturated with phenol

A second 400.13 g of the aqueous condensate was extracted, first with 28.2 g of the phenol layer from the second stage of the extraction shown in Table 12, then with 29.22 g of the phenol layer from the third stage of the extraction shown in Table 12 and finally with 20.60 g of fresh high purity phenol. Three 2.2 g samples of the aqueous layers were removed for analysis after the first, second and third extractions.

The size and impurity levels (in ppm) on analyses of layers removed from each extraction are shown in Table 13.

TABLE 13

| Extraction | Layer | Size (g) | Total Impurities | Acetone | AP | MBF | Others |
|---|---|---|---|---|---|---|---|
| 1 | Phenol | 13.9 | 12,612 | 7120 | 4610 | 89.2 | 793 |
| 2 | Phenol | 23.9 | 5,583 | 4471 | 945 | 14.1 | 153 |
| 3 | Phenol | 30.3 | 3,303 | 3079 | 183 | ND | 41 |
| 1 | Aqueous* | 414.4 | 897 | 829 | 56 | ND | 12 |
| 2 | Aqueous* | 417.6 | 695 | 680 | 10 | ND | 5 |
| 3 | Aqueous* | 405.6 | 495 | 490 | 2 | ND | 3 |

This second series of extraction simulates counter-current extraction in three stages. It is apparent from these runs that extraction with small quantities of high purity phenol is an effective method for reducing the impurity content of the aqueous condensate. Accordingly, return of the condensate to the azeotropic distillation column should be about as effective as fresh water feed, as shown in Example 3.

Example 5—Chlorination Colors

Chlorination colors were taken of the high purity phenol products from Product Runs D–L, N and P, above. Chlorination colors were measured by the tests described in U.S. Pat. No. 2,992,169 (July 11, 1961). Runs E, F and G were continuous product distillation runs; all others were batch.

The absorption spectrum showed a peak at 490 nm (millimicrons) which was higher than values conventionally taken at 510 or 540 nm. The optical densities ranged from 0.137 to 0.341 for these runs. Optical densities compared to total impurity and MBF concentration for these runs are shown in Table 14.

TABLE 14

| Product Run | Impurity Content: Total vs. MBF (ppm) | O.D. at 490 nm | O.D. at 510 nm | O.D. at 540 nm |
|---|---|---|---|---|
| D* | 17/2 | 0.171 | 0.141 | 0.107 |
| E* | 31/10 | 0.341 | 0.263 | 0.165 |
| F* | 14/4 | 0.341 | 0.294 | 0.212 |
| G* | 8/5 | 0.202 | 0.166 | 0.108 |
| H** | 12/5 | 0.178 | 0.151 | 0.121 |
| I** | 14/7 | 0.147 | 0.120 | 0.086 |
| J** | 10/4 | 0.137 | 0.109 | 0.081 |
| K** | 20/8 | 0.149 | 0.127 | 0.105 |
| L** | 21/9 | 0.222 | 0.181 | 0.129 |
| N*** | 16/2 | 0.243 | 0.168 | 0.079 |
| P*** | 18/0 | 0.194 | 0.138 | 0.068 |

*Refined phenol as starting material followed by azeo distillation with fresh water.
**Refined phenol as starting material followed by azeo distillation using recycled cumene extracted azeo water.
***Low grade phenol as starting material followed by azeo distillation with fresh water.

What is claimed is:

1. In the process of purifying phenol produced by the cleavage of cumene hydroperoxide wherein the feed phenol is treated with a base, the treated phenol is steam distilled to remove a lites fraction as a water azeotrope and the bottoms of the steam distillation are distilled to recover high purity phenol as an overhead; the improvement wherein the overheads of the steam distillation are condensed and organics are extracted with an organic solvent which preferentially dissolves benzofuran impurities to produce a reflux aqueous phase and the reflux aqueous phase is returned to the steam distillation.

2. The process of claim 1 wherein the condensed overheads are phase separated into an aqueous layer and an organic layer and only the aqueous layer is extracted with the organic solvent.

3. The process of claim 1 wherein the entire condensed overheads are extracted with the organic solvent to produce the reflux aqueous phase.

4. The process of claims 1 or 2 or 3 wherein the extraction is multiple stage.

5. The process of claims 1 or 2 or 3 wherein the organic solvent is cumene, toluene or a xylene.

6. The process of claim 5 wherein the organic solvent after extraction is washed with an aqueous base to remove phenol and impurities and the organic solvent recovered is used again to extract organics.

7. The process of claim 1 or 3 wherein said organic solvent is high purity phenol.

8. The process of claim 1 wherein said treated phenol has between about 30 and about 150 ppm methylbenzofuran by weight as an impurity and wherein sufficient steam is distilled with said treated phenol to reduce methylbenzofuran to below about 25 ppm in said high purity phenol.

9. The process of claim 1 or 8 wherein said feed phenol is treated with a polyamine as base and then sufficient phthalic anhydride per mol of polyamine is added prior to steam distillation to lower the pH of said chemically treated phenol to between about 4.0 and about 5.5.

10. The process of claim 1 wherein an acid anhydride is added after the feed phenol is treated with a base.

* * * * *